United States Patent [19]

Hanss

[11] 4,348,890
[45] Sep. 14, 1982

[54] APPARATUS AND A PROCESS FOR DETERMINING THE RHEOLOGICAL PROPERTIES OF BIOLOGICAL FLUIDS

[76] Inventor: Maxime F. Hanss, 2 Allée de la Mairie d'Antan, Saint Witz, 95470 Survilliers, France

[21] Appl. No.: 175,329

[22] Filed: Aug. 4, 1980

[30] Foreign Application Priority Data

Aug. 17, 1979 [FR] France .................................. 79 20833

[51] Int. Cl.³ .......................................... G01N 15/04
[52] U.S. Cl. ...................................................... 73/61.4
[58] Field of Search .......................... 73/61.4, 55, 61 R

[56] References Cited

U.S. PATENT DOCUMENTS

| | | | |
|---|---|---|---|
| 2,572,436 | 10/1951 | Boucher et al. | 73/61.4 |
| 2,786,977 | 3/1957 | Blagg et al. | 73/61.4 X |
| 3,604,247 | 9/1971 | Gramain et al. | 73/55 |

FOREIGN PATENT DOCUMENTS

| | | | |
|---|---|---|---|
| 2405839 | 8/1975 | Fed. Rep. of Germany. | |
| 2431129 | 3/1980 | France | 73/61.4 |
| 53-47807 | 7/1978 | Japan | 73/55 |
| 587484 | 5/1977 | Switzerland | 73/61.4 |

Primary Examiner—Anthony V. Ciarlante
Assistant Examiner—Joseph W. Roskos
Attorney, Agent, or Firm—Browdy & Neimark

[57] ABSTRACT

An apparatus for determining the filterability of red blood cells comprises a first upper transparent block containing at the center a capillary having an inner diameter between 1 and 10 mm, which block is provided with two level detectors; a second lower transparent block, provided with a central duct—facing the capillary of the upper block—inside which duct is housed a drop-taking device, such duct being connected on the one hand to a drain circuit and on the other to a pressure regulating circuit; a filtering membrane housed between the two blocks and a frame for holding the apparatus. First the initial mean flow time of the serum is measured, then the initial mean flow time of a volume of the suspension of cells in the plasma at a given concentration using such apparatus, and then the index of filterability is calculated.

21 Claims, 8 Drawing Figures

APPARATUS AND A PROCESS FOR DETERMINING THE RHEOLOGICAL PROPERTIES OF BIOLOGICAL FLUIDS

BACKGROUND OF THE INVENTION

The present invention relates to an apparatus and a process for determining the rheological properties of biological fluids, and particularly for determining the filterability of cells in suspension and the viscosity of biological liquids. It relates more particularly to an apparatus and a process for determining the deformability of the red corpuscles of the blood. The biconcave and disk-like lens shape of the red corpuscle ensures for this latter (which has a diameter of about $7.5\mu$), the elasticity or the deformability required to allow it to pass through the circulatory ducts of the organism some of which scarcely exceed 2 to $3\mu$ in diameter). The role of the deformability of the red corpuscles in circulatory and more precisely microcirculatory physiology, is now well-known (sometimes, it is the only means for detecting certain anomalies of the blood which are at the origin of different illnesses) and so it is very important to be able to measure this deformability. Further, this measurement (necessarily made in vitro) must accurately reflect and exactly translate this important quality of the red corpuscle, it must be accurate, reliable and reproducible, and it must be also as simple and as economical as possible, so as to be able to be used on a large scale not only in laboratories for biological analyses but also in research laboratories.

Numerous methods have been proposed for determining and measuring the deformability of the red corpuscle. Thus, the following have been used:—measurements of suction and flow in capillary tubes and micropipettes;—viscosimetric techniques;—microscopic examinations, after transformation of the erythrocytes by means of chemical agents;—measurements by light diffraction;—compression studies of the centrifugation button;—sedimentation and centrifugation backing measurements;—studies of the extension of the fixed corpuscles, on a microthread;—and the filtration or more exactly the filterability of the red blood corpuscles.

For example, the following have been advocated:

measurement of the deformability by the suction technique through a micropipette [RAND and BURTON (Bioph. J. 4, 115 1964)], by means of which the length of the "finger" of the membrane of the sucked-up corpuscle is measured. Though insofar as the principle and results are concerned, this technique gives satisfaction, this measurement is still only practised exceptionally because of its difficulty and its duration which is rather long;

viscosimetric measurements (by means of a capillary or rotary viscosimeter).

Generally, all the measurements advocated [compare in particular the work of CHIEN et alia, Biorheology 12, 341, 1975; of THURSTON (Biophys. J. 12, 1205, 1972) and of USAMI et alia (Biorheology 10, 425, 1973)] are based on the concept according to which the viscosity of suspensions measured at a high speed gradient is smaller when the particles are deformable. However, such determinations are not very sensitive and very often require costly apparatus not very convenient to handle.

techniques of microscopic examination of the corpuscles; these techniques concern the microscopic examination of the cells in a flow of the Poiseuille type (for example in a capillary or in a transparent cone-flat viscosimeter). It is a very delicate technique which requires complex apparatus and whose results may sometimes be unreliable: the cells must in fact be placed in suspension in a very viscous nonphysiological medium (compare the "Rheoscope" by SCHMID-SCHÖNBEIN).

The results are also difficult to interpret, even after having fixed the shape of the cells by means of chemical agents such as glutaraldehyde or acetaldehyde.

techniques of indirect visualization of the deformation by studying the images of the diffraction of light.

This technique, studied more particularly by BESSIS and MOHANDAS [Blood Cells. 3 229–239 (1977) and Blood Cells 1 307–313 (1975)] also measures the extension of the cells subjected to shearing stresses, by using the diffraction of light (and particularly the diffraction of a laser ray passing through the blood sample).

These methods of measurement, besides being slow and not very well adapted to industrial measurements, require furthermore very costly apparatus whose handling is delicate: the cells must always be placed in a very viscous medium, very different from the physiological conditions.

methods based on filtration.

Among the very numerous methods used for estimating the erythrocytary deformability, filtration is perhaps the only one which, up to date, has known a great extension, probably because of its simplicity.

The general principle for determining the erythrocytary filterability is the measurement of the flow of a suspension of red corpuscles concentrated to a greater or lesser degree through a membrane whose pores have a mean diameter less than that of the red blood corpuscles. For a given membrane and motive pressure, the filtration flow will be all the smaller the more difficult it is for the red blood corpuscles to be deformed.

The filtration flow is given by:

$$D = dV/dt \quad (1)$$

where dV is the volume of liquid passing through the filter during the time dt. If this latter is not small enough for the flow to be constant, the measured flow is a mean flow given by:

$$D = \Delta V / \Delta T \quad (2)$$

Generally, the mean flow measured between two times $t_2$ and $t_1$ (such as $t_2 - t_1 = \Delta t$) will be expressed by the relationship (3) below:

$$D = 1/\Delta t \int_{t_1}^{t_2} D dt \quad (3)$$

An examination of the relationship (3) shows that the mean and instantaneous flows are only identical when D is independent of time (constant flow rate). For a membrane, the filtration flow is the sum of the elementary flows through each pore of the membrane.

If d represents the value of the flow rate of an homogeneous fluid of viscosity $\eta_o$ through a pore of a porous membrane of unit area, and l the length of the axis of the pore (assumed perpendicular to the surface of the filtering membrane) which forms the thickness of this membrane, and if r is the radius of the pore, we have (Poiseuille's relationship)

$$d = \frac{\pi}{8\eta_o} r^4 \frac{P}{l}$$

P representing the pressure difference between the inlet and the outlet of the pore.

If $N_o$ represents the number of pores of the membrane at time $t_o$, we then have:

$$D = N_o d = N_o \frac{\pi}{8\eta_o} r^4 \frac{\Delta P}{l} \quad (4)$$

For example, for a typical membrane of the trademark "NUCLEPORE" (manufactured by the GENERAL ELECTRIC COMPANY)
(where
r = 2.5μ
l = 12μ
$N_o = 4.10^5/cm^2$
and for a liquid such as water at 25° C. ($\eta_o = 0.01$ poise), we have D≃1 cm³/second for L cm² of membrane.

Based on this data, a large number of methods and apparatus have been described for measuring the filtration or more exactly the filterability of red corpuscles. In particular:

S. CHIEN et alia [Biorheology 8, 163 (1971)] measure the percentage of cells which pass while applying a pressure gradient;

L. S. LESSIN et alia [Blood Cells 3, 241–262 (1977)] also use a positive pressure through the "NUCLEPORE" membrane while using a very complicated apparatus;

SCHMID-SCHÖNBEIN et alia [Blut (1973) 26, 369–379], and REID H. L. et alia [J. Clin. Pathol. (1976) 29(9), 855–858] use on the other hand a simple device allowing a vacuum (about 20 cm of water) to be ensured, to which is connected a filter-support able to receive a filtering "NUCLEPORE" membrane made from polycarbonate having a diameter of 13 mm, whose cylindrical pores have a diameter of 5μ. A 1 ml syringe may be adapted to the filter-support. The filterability of the red blood corpuscles in a 40% suspension in physiological serum is assessed by timing the time taken for 1 ml of suspension to pass;

P. TEITEL [Nature (Lond.) 184, 1808 (1959), Sangre (Barcelona) 9, 282 (1964), Blood Cells 3, 55–70 (1977)] advocates quite simply a paper filter (the pore diameters range between 20 and 40μ), the only pressure exerted being gravimetric, the measurement being effected by determining the flow rate of the liquid (a suspension of washed red blood corpuscles, whose hematocrit is greater than 90%) through the filter.

It should be noted that the use of the "NUCLEPORE" filter as a model for the capillary was already advocated in 1966 [GREGERSEN et alia "Hemorheology" (Copley Ed.) Pergamon Press. Oxford].

As can be seen from the above, all the techniques proposed in the prior art do not comply with the criteria which require an analysis to be at one and the same time simple to carry out, economical, accurate, reproducible and reliable, and to "measure" perfectly the properties of the red corpuscles represented by their flexibility, their elasticity and their deformability.

It is clear, in examining the relationship (4) above, that to have accurate, reliable and reproducible measurements and especially to have measurements which correspond to the reality of the facts, i.e. which are indeed connected with this essential mechanical quality of the red blood corpuscles formed by the deformability, a certain number of parameters must be reconsidered and restated.

(1) GEOMETRIC FACTORS

In a well-designed filter, and this is not always the case, it may be assumed that the total number of pores accessible to the fluid at a time $t_o$ is constant from one membrane to the other. Similarly, possible variations of the thickness of the membrane between two measurements may be disregarded. On the other hand, the role of the fluctuations of the mean diameter of the pores must be discussed further. Such fluctuations could occur for thermal or mechanical reasons (expansion of the pores because of excess tension in the membrane), or for reasons due to the manufacture itself (paper filters for example). The examination of Poiseuille's law shows that r is to the power of 4. If for example, r passes from 2.5 to 2.6μ, the flow rate will increase by 17%.

(2) MOTIVE PRESSURE OF THE FLOW

At the beginning of filtration (effected for example in a vacuum for a pressure P less than the atmospheric pressure $P_o$), the pressure at the level of the upper surface of the membrane will be equal to $P + \Delta P$, and the motive force which determines the flow of the liquid through each pore will be $\Delta P \times \pi r^2$.

Assuming all the other factors constant, Poiseuille's law may be written in the following form:

$$D = \frac{dV}{dt} = K \Delta P \quad (5)$$

the constant K being:

$$K = N_o \frac{\pi}{8\eta_o} \frac{r^4}{l}$$

If at time t the height of the liquid to be filtered is equal to h, the $\Delta P$ is obtained by applying Pascal's law $$P = \rho g(h + h')$$

where
ρ = the specific mass of the liquid to be filtered
g = the acceleration of gravity
and
h' = the depression expressed in cm of water.

Now, $\Delta P$ diminishes constantly during filtration, because of the drop in the level. If the tube containing the suspension to be filtered whose level is $h_o$ at the initial time $t_o$ has a section S; and if the initial volume of the solution to be filtered is designated by $V_o$ and if the volume of the liquid which is filtered at time t is designated by V, the motive pressure will then be:

$$\Delta P = g = \frac{V_o - V}{S} + h'$$

If the expression of $\Delta P$ is incorporated in relationship (5), an expression is obtained which gives the flow volume V at each instant:

$$V = S(h' + h_o)(1 - e^{-\frac{K}{S}\rho g t}) \quad (6)$$

This expression indicates that the flow volume increases less and less quickly, i.e. that the flow rate decreases regularly, during the whole of the filtration.

(3) PROBLEMS CONNECTED WITH THE SURFACE TENSION

It is well-known that, when an empty capillary having an internal radius r is plunged into a liquid, the level will be different from that of the liquid on the outside of the tube. If the liquid damps the wall, the liquid will rise in the capillary, it will descend in the opposite case. The final difference in level reached $h_S$ is given by JURIN's law:

$$h_S = \frac{2A}{\rho g} \cdot \frac{\cos \theta}{r} \qquad (7)$$

where:
$\rho$: specific mass of the liquid
$A$: surface tension of the liquid
$\theta$: angle of connection between the liquid and the internal wall of the capillary. If $\theta = 0$, the liquid damps perfectly the solid; if $\theta = 180°$, the damping is zero. Angle $\theta$ depends on the nature of the liquid and of the capillary; for plastic materials (such as polycarbonate) and water, $\theta$ is greater than 90°.

If a tube made from plastic material having an inner diameter of 1 mm is plunged into water, it can be seen that $h_S$ is of the order of 1 cm, and negative. That means that a depression of 1 cm of water would need to be exerted in order to remove the difference in level. If JURIN's law is applied for an elementary pore of the membrane, and admitting the preceding figures, it can be deduced that the pressure difference required for causing the liquid to flow through this pore would be about 200 cm of water. In reality, different factors come into play to reduce this extreme value; this figure indicates nevertheless the very important role that the interfacial phenomena may have in filtration. This result explains why it is sometimes necessary to apply a brief overpressure to cause the flow to start. With this begun, the liquid spreads over the other face of the membrane and JURIN's law no longer applies to capillaries of 5$\mu$ in diameter, but to a duct having an ill-defined section, represented by the gaps between the membrane and the membrane support, as well as by the section of the orifices of the membrane support. Certain important differences observed when filtering several times the same sample may be explained by differences in the position of the membrane with respect to its support from one analysis to the other.

Another consequence of the surface phenomena is the blocking of the flow by microbubbles inside the pores or between the lower face of the membrane and its support. In fact, if a gaseous bubble fills a portion of the capillary, it will be necessary here again to exert an additional pressure equal to (2A/r) to cause this liquid to flow. This explains why certain authors advocate using filtration measurements by plunging the device into a large volume of degassified water.

It should also be noticed that the phenomenon of capillarity may be introduced into the relationship (5) in the form of a reduction of $\rho g h'$:

$$\Delta P = \rho g h + \left(h' - \frac{2A}{r} \cos\theta\right)$$

Referring to relationship (6), it can be seen then that the errors made by confusing $t_1$ and $t'_1$ ($t_1$ being the real time for draining the tube containing the liquid and $t'_1$ being the time for draining the tube if $\Delta P$ were constant) may become important. Furthermore, these errors will be random, for the capillarity term depends on uncontrollable factors, such as the surface condition of the membranes, of the pores, of the membrane support, the position of the membrane with respect to the support, etc.

(4) NUMBER OF EFFECTIVE PORES

In Poiseuille's relationship (relationship 4), $N_o$ represents the number of pores per unit area of the membrane.

This factor is not constant during filtration, and the origin and the consequence of these variations should be studied.

(a) Problems connected with the filter support

Generally, the membrane is placed on the support. This stops up a fraction $\alpha$ of the pores, so that the number of pores really effective at time $t_o$ is $(1-\alpha)N_o$. It is possible, in some cases, that $\alpha$ differs from one experiment to another (for example because of puckering of the membrane, or of deformations of the support, or of the equality of this latter).

The result will then be variations of the filtration times, all else being equal.

(b) Problems connected with the clogging up of the filter

Some cells of the suspension may clog up the pores of the filter. This results in progressively reducing $(1-\alpha)N_o$.

In other words, the flow rate is a decreasing function of time. If $c'$ is the concentration of the cells in question, and in assuming in Poiseuille's relationship (4), all other factors except $N_o$ constant, we will then write $D = K_1 N$.

If we admit that a pore is clogged up each time that a cell is engaged therein, the number of pores which clog up during time dt will be $dN = c'dV$ or $$dN = c'dt$$

The variation of the flow rate may be deduced therefrom:

$$dD = -K_1 c' D dt$$

The flow rate will then be a function of time. If $D_o$ is the initial value, the flow rate at time t will be given by a law of the type:

$$D_t = D_o e^{-K_1 c' t} \qquad (8)$$

where $$K_1 = \frac{\pi}{8\eta} (1-\alpha) \frac{r^4}{l} \Delta P$$

The origin of the clogging up may be variable. The white corpuscles pass only with difficulty through the pores usually used, and it is essential to eliminate them so that the filtration times measured are characteristic of the red blood corpuscles alone.

Besides the platelet aggregates eliminated with the white corpuscles, the rollers and erythrocytary aggregates may also, in principle, stop up pores. In this case, an extension of the filtration time comes from the interactions between cells and not from modifications of their rheological properties. The importance of this clogging-up mechanism is however very difficult to estimate, for the shearing stresses at the inlet to the pore may be sufficient to break up these aggregates.

Finally, the clogging-up may come from a high rigidity of the red blood corpuscles. In this case only, the progressive reduction in the flow rate is an interesting magnitude to measure, signicative of the erythrocytary rheology. But it must again be emphasized that this phenomenon is only desirable if care has been taken to eliminate the other causes of clogging up.

(5) ROLE OF THE VISCOSITY

In Poiseuille's relationship (4), the flow rate is inversely proportional to the viscosity of the fluid. For the usual liquids, in particular water, the physiological serum, as well as for plasma, the viscosity depends greatly on the temperature T: the viscosity diminishes by about 2% when the temperature increases 1° C. It is then advisable to avoid temperature differences greater than 5° C. from one operation to another, if the temperature error is to remain less than 10%.

When a filtration operation is considered macroscopically, the presence of the red blood corpuscles in this fluid to be filtered reduces the overall flow rate.

This may lead to an increase in the resistance to flow due to an increased viscosity of the medium.

(6) ROLE OF SEDIMENTATION

The filtration flow rate depends on the effective concentration in the neighborhood of the pores (c). It may be confused with the mean concentration of the suspension only at the moment of filling the filtration tube, or else if there exists an efficient agitation during the whole of the filtration, which is practically never the case.

This effect is even more important when whole blood is studied at a high sedimentation rate (VS). For diluted blood, the increase of the VS of the blood causes less variations in the filtration time, for the red blood corpuscles sediment much more independently from each other without forming rollers and aggregates. Nevertheless, and even in this latter case, the sedimentation will cause an accumulation of the red blood corpuscles on the upper face of the membrane in a short time (typically of the order of a few tens of seconds). The result is that all the measurements based on the filtration of a large volume of blood (so long) will be affected in variable and uncontrollable proportions by this phenomenon.

SUMMARY OF THE INVENTION

The aim of the present invention is then to provide an apparatus for measuring the filterability of red corpuscles, which answers better the requirements of practice than previously known apparatus having the same aim, particularly in that is makes the measurement reproducible and perfectly reliable, insensitive to the progressive clogging up of the filter, insensitive to the sedimentation which may take place on the surface of the filter; in that it allows measurements to be carried out with good accuracy; in that it is easy of access and easy to handle; in that it avoids stopping up of a part of the membrane, which is no longer in contact with a rigid support, as is the case in the apparatus of the prior art; in that it avoids the microbubble phenomenon which occurs in most of the apparatus of the prior art between the lower face of the filtering membrane and the upper face of the support; in that it promotes flow of the liquid and considerably reduces the influence of temperature variations and of the viscosity of the solvent; in that it allows the filtering membranes to be used many times thus reducing the cost of the measurement and in that it allows other rheological properties—other than deformability—to be measured, such for example as viscosity.

The present invention provides an apparatus for determining the rheological properties of biological fluids, and particularly the deformability of the red corpuscles of the blood, characterized in that is comprises, in combination:—a first upper transparent block containing in its center a capillary with an inner diameter between 1 and 10 mm, which block is provided with two level detectors;—a second lower transparent block provided with a central duct—facing the capillary of the upper block—inside which duct is housed a drop-taking device, said duct being connected on the one hand to an draining circuit and, on the other hand, to a pressure-regulating circuit;—a filtering membrane housed between the two blocks and—a frame for holding the apparatus.

According to an advantageous embodiment of the apparatus of the invention, the filtering membrane rests on a filter-paper, whose diameter is slightly greater than that of the membrane.

According to another advantageous embodiment of the apparatus of the invention, the two level detectors are housed one below the other and spaced apart from about 1 to 20 mm.

According to a particular procedure of this embodiment, said level detectors are optical detectors formed by a light emitter and a receiving photodiode (or phototransistor).

According to another procedure, the optical detector is formed by an optical fiber connected to a light source and an optical fiber connected to a receiving photodiode (or phototransistor).

In accordance with the invention, the two level detectors are connected electronically to a timer for measuring the filtration time: the upper detector for starting, the lower level detector for stopping the timer.

In accordance with the invention, the lower block is movable and slides along two guide rods situated on each side of the central cavity, said guide rods being maintained, on the one hand, on the low part of the upper block which is made integral with the frame, said low part being flared with respect to the body of the upper block and, on the other hand, by their lower end on the frame of the apparatus.

Since the guide rods are simply held in two apertures of the base of the frame, they can be very easily withdrawn to readily free the lower block if it is desired to clean it.

According to an advantageous embodiment of the invention, the low part of the capillary is bell-shaped and has a diameter substantially equal to that of the central cavity of the lower block, and slightly less than the diameter of the filtering membrane.

According to a particularly advantageous procedure, the bell-shaped part of the capillary or the upper face of the lower block are provided with seals for maintaining the filtering membrane.

In accordance with the invention, two springs are fixed by one of their ends to the lower block, the other end of these two springs ending in a hook which engages in two small notches or recesses (one per spring)

provided for this purpose in the bell-shaped low part of the upper block.

The two springs stretched during the filtration operations ensure the tightness of the system, as well as the stability of the apparatus and thus facilitate the filtration operations. The association of the guide rods with the springs, easy to position and to remove, allows rapid and reliable operation of the filtration apparatus, and avoids the filtration membrane having to withstand shearing stresses or risks of movement when the two blocks (lower and upper) and brought closer together.

According to an advantageous embodiment of the apparatus of the invention, the drop-taking device is formed by a rod made from glass, a plastic material, metal or similar, integral with the lower block and fixed to the bottom of said lower block by a seal and/or a ring made from a resilient and sealing material.

This rod may have any desired shape: it may end in a point, a sphere, a vault having the form of a mushroom, etc.

According to a particularly advantageous procedure, the drop-taking rod is covered on its upper part, which is in contact with the filtering membrane, with a strip of filter-paper straddling the end of said rod.

According to another particular procedure, the drop-taking rod is formed by a cylinder having laterally therethrough numerous holes which are filled with a water-absorbing material.

The purpose of the device in accordance with the preceding arrangements is to facilitate the filtration, make the initial filtration time as short as possible and to cause the filtration to depend only on the power of deformability of the red corpuscles examined.

According to another advantageous embodiment of the invention, the pressure control circuit comprises:
- a three-way cock communicating the central duct of the lower block either with an overpressure ballast-receptacle, or with a "measure" circuit;
- a ballast-receptacle of a capacity between 0.1 and 5 liters, provided with a device for creating a small overpressure (0 to 50 cm of water) which may be a syringe or a pear-shaped bulb fitted with a valve, a receptacle filled with liquid which is raised, or similar;
- a "measure" circuit formed:
- either by a simple tube open to the atmosphere, if it is desired to filter only with the hydrostatic pressure of the liquid filling the capillary of the upper block,
- or by a tube connected to a second ballast-receptacle of 0.1 to 5 liters, having a vacuum inlet pipe if it is desired to filter with a depression. Here again the partial vacuum may be obtained by means of a syringe or a pear-shaped bulb fitted with a valve, a receptacle filled with liquid which is lowered, or similar.

In accordance with the invention, setting a three-way cock to the "measure" circuit is electronically connected to the timer for counting down the filtration time so as to reset it automatically.

According to an advantageous embodiment of the invention, the capillary situated in the center of the upper block forms an integral part of the mass of said upper block and is manufactured in one piece therewith.

According to another advantageous embodiment of the invention, the capillary situated in the center of the upper block is introduced into a wider duct provided for this purpose and bonded against the wall of said duct.

The present invention also provides a process for determining the rheological properties of biological fluids, and particularly a process for measuring the filterability of the red corpuscles of the blood by means of the apparatus in accordance with the present invention, which process is characterized in that the initial mean flow time of the solvent (physiological serum, plasma or similar), then the initial mean flow time of a volume of the suspension of a given concentration to be examined is first of all examined and in that the filterability index is determined by applying formula (9) herebelow:

$$I_f = \frac{tg - ts}{ts \times H} \qquad (9)$$

where:

$I_f$: index of filterability $ts$: initial mean flow time of the solvent $tg$: initial mean flow time of the suspension of corpuscles to be examined, and $H$: voluminal mass concentration (V/V) of the red blood corpuscles in the suspension or hematocrit.

Besides the above arrangements, the invention comprises still other arrangements which will become clear from the following description.

The invention will be better understood with the help of the complement of description which follows, which refers to embodiments of the apparatus in accordance with the present invention, shown in the accompanying drawings, as well as to an example of measuring the deformability of the red corpuscles.

It will however be readily understood that the arrangements described in what follows and shown in the drawings, as well as the example of implementing the process in accordance with the present invention, are given solely by way of illustration of the object of the invention, but constitute by no means a limitation thereof.

DESCRIPTION OF THE DRAWINGS

The apparatus of the present invention which provides determinations of the rheological properties of biological fluids and particularly the measurement of the deformability of the red corpuscles by filtration, will now be described with reference to the accompanying drawings, in which.

DESCRIPTION OF THE PREFERRED EMBODIMENTS

Figure 1:
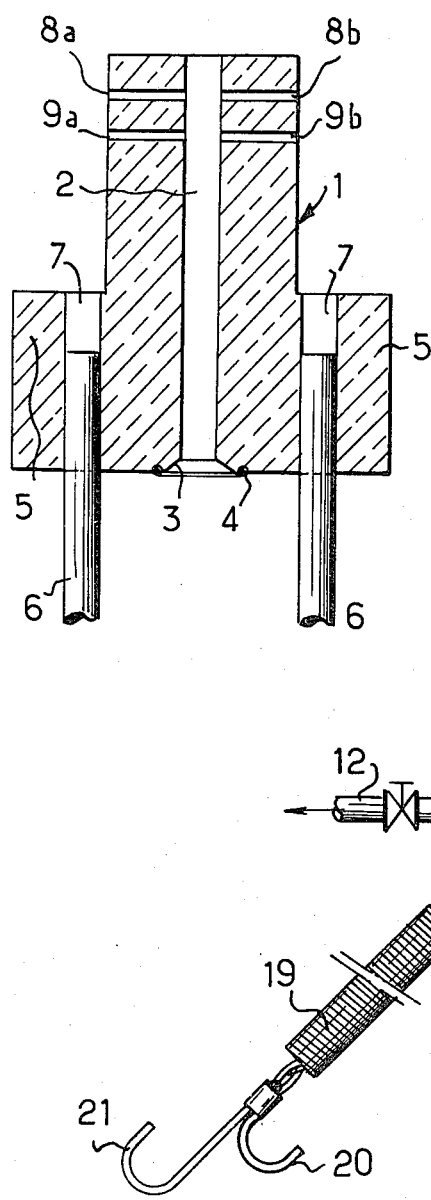
FIGS. 1, 2 and 3 show schematically the three parts of the apparatus: the upper block, the lower block and the pressure control device.

FIG. 1 shows in section the upper block 1, made from a transparent plastic material, in the center of which is the capillary 2 whose low bell-mounted part 3 is provided with an O-joint 4 which bears against the filtering membrane and the lower block. Guide rods 6 slide in the lower bell-shaped part 5 of the upper part 1, which comprises two notches 7 where are engaged the hooks of the upper end of holding springs. The level detectors 8 and 9 are housed in the upper part of the upper block 1; 8a and 9a represent the light emitters, 8b and 9b the emitted-light receivers (diodes or optical fibers). The distance between the upper light detector and the lower light detector varies between 1 and 20 mm, and depends on the viscosity of the fluid to be filtered, the dimensions of the level detectors and the resolution of the timer.

Figure 2:
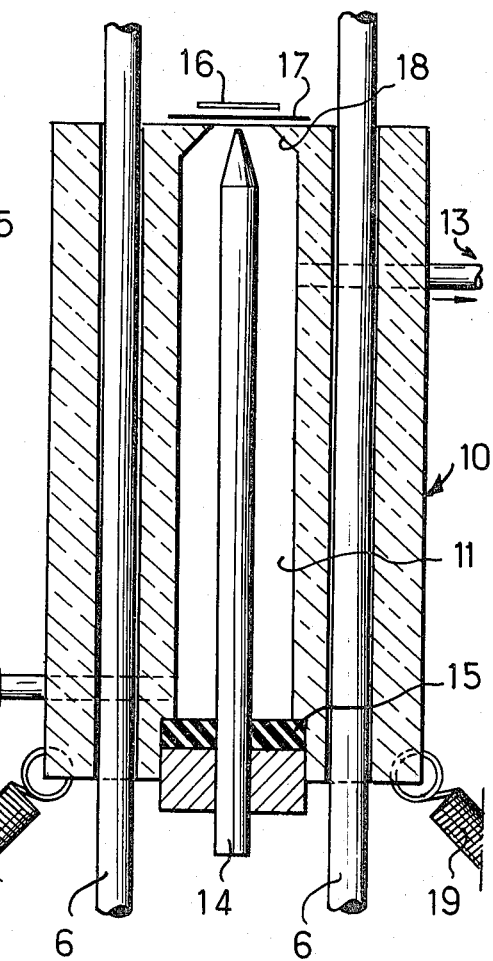

FIG. 2 shows in section the lower block made from a transparent plastic material 10 with its central duct 11 connected, on the one hand, to the drain 12 and, on the other hand, to the pressure-control circuit 13. The drop-taking rod 14 is placed in the center of the duct and is fixed to the lower block by means of a sealing member 15. The filtering membrane 16 and the filter-paper washer 17 disposed below said membrane 16, are placed above duct 11 which has a slight narrowing 18. The two holding springs 19 are fixed to the lower part of lower block 10 and they are provided at their free end with two hooks: hook 20 which engages in notch 7 provided for this purpose in the upper block 1, and the grasping hook 21. The two guide rods 6 placed on each side of the central duct 11 allow longitudinal sliding of lower block 10, to bring it nearer or move it away from the fixed upper block 1, made integral with the frame.

Figure 3:
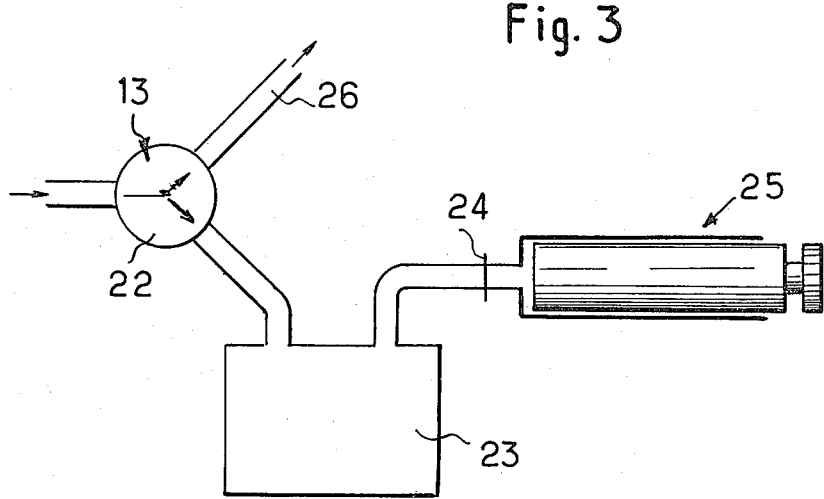

FIG. 3 shows schematically the pressure-control device 13. It comprises essentially the three-way cock 22 connected either to the "measure" circuit 26, or to syringe 25 (of a capacity of 2 to 50 ml), by means of the ballast-receptacle 23 and valve 24. With this syringe 25, an overpressure is created in the apparatus. It is obvious that the syringe may be replaced by a pear-shaped bulb for example, or even simply by a receptacle filled with liquid which is raised.

The electronic circuit which connects the measuring timer to the "measure" outlet of cock 22 and to the two level detectors 8 and 9, is not shown in the figures.

Figure 4:
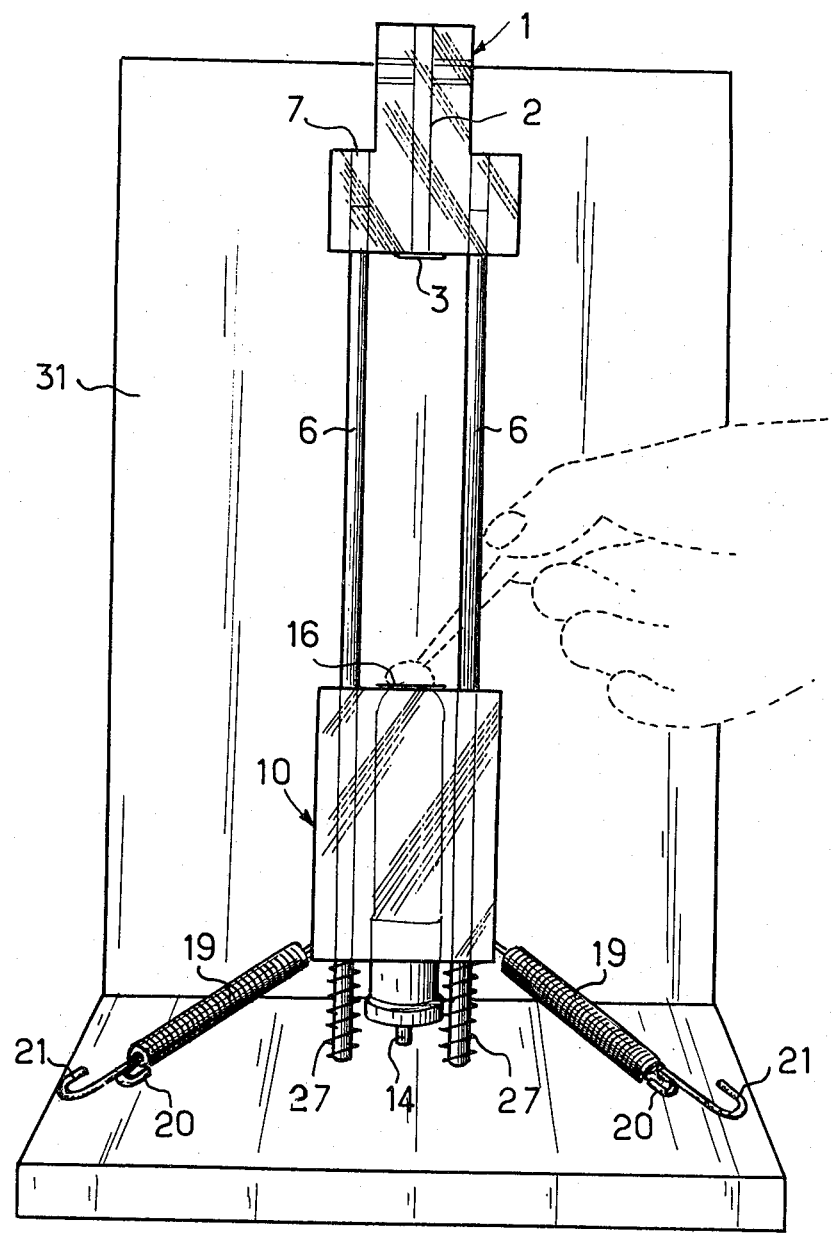
FIGS. 4 and 5 show the apparatus—seen from the front—in an open position, with the two blocks separated (FIG. 4) and in a closed position, ready for use (FIG. 5)

FIG. 4 shows the apparatus of the invention, seen open in a front view, the two springs 19 being placed on the base of frame 31, and the two blocks 1 and 10 being separated. Block 1 is fixed and is made integral with frame 31, whereas block 10 slides along guide rods 6, said rods being held in two apertures provided in the base of frame 31. Block 10 rests in the open position of the apparatus on two supporting springs 27. There is shown in FIG. 4, a method for placing the filtering membrane 16 above the lower block 10. The bell-shaped part 3 of the capillary 2 bears against filtering membrane 6 at the moment of closing the apparatus.

Figure 5:
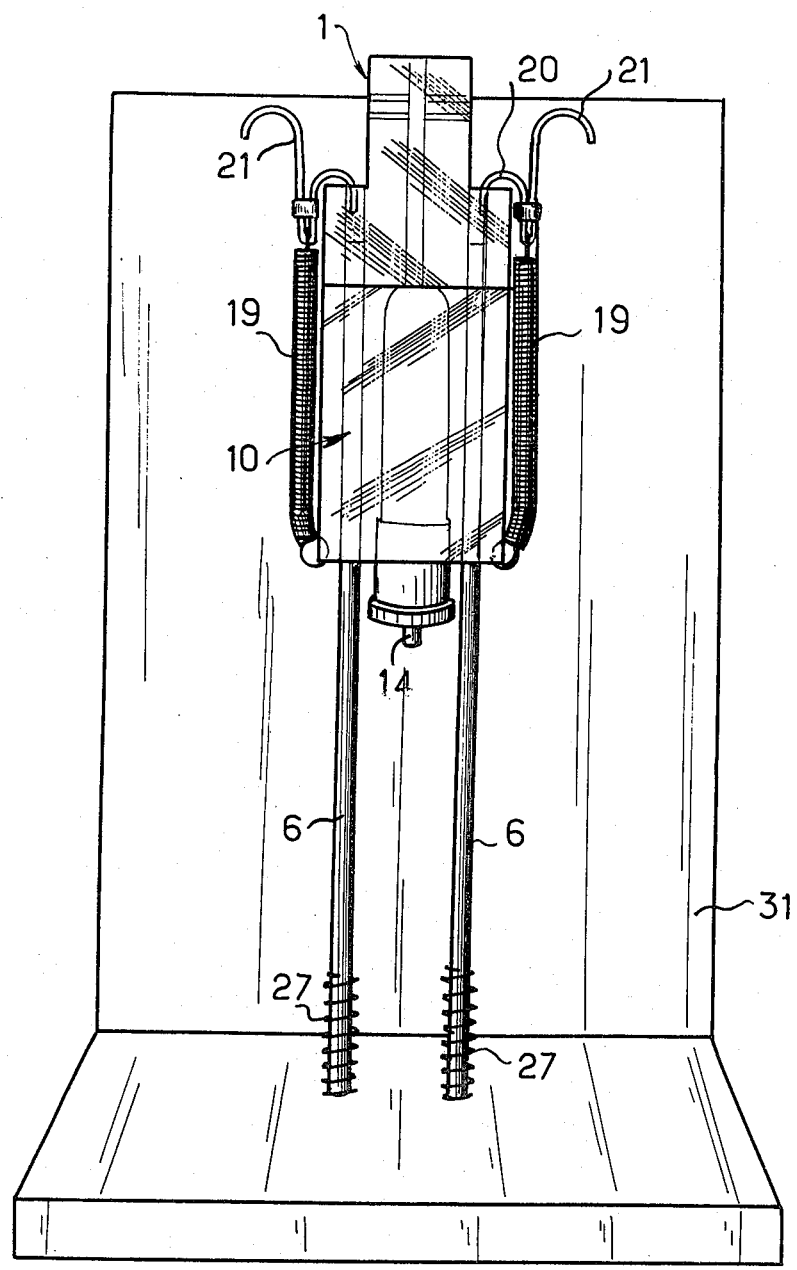

FIG. 5 shows the apparatus of the invention closed, ready to use. The two springs 19 are stretched, hook 20 being engaged in the corresponding notch 7, the two blocks 1 and 10 are adjacent to each other.

FIG. 6 shows in a non-limiting way three variations of droptaking rods.

Figure 6A:
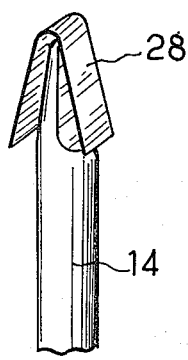
FIGS. 6a, 6b and 6c show three different variations of drop-taking rods.
Figure 6B:
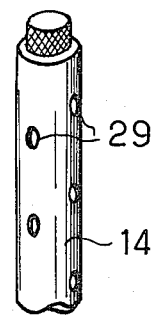
Figure 6C:
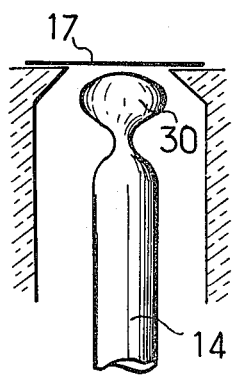

FIG. 6a shows a rod 14 made from stainless steel ending in a bevel on which there is placed—astraddle—a strip of filter-paper 28. FIG. 6b shows a rod 14 in the form of a cylindrical tube having holes 29, filled with water-absorbing fibers. FIG. 6c shows a rod 14 made from glass, ending in a bell-shaped part 30 having substantially the shape of an eggs, which bears against the filter-paper washer 17 placed below filtering membrane 16. Other forms are obviously possible.

There will be found hereafter a non-limiting example of measuring the filterability of red blood corpuscles in accordance with the process of the present invention.

I. EXAMPLE OF DETERMINING THE FILTERABILITY OF THE RED BLOOD CORPUSCLES

With the apparatus open, and the two blocks 1 and 10 separated, a small strip of filter-paper 28 (4 mm in width and 7 cm in length) is placed astride the upper end of the drop-taking rod 14. This strip of filter-paper is previously damped with the solvent (physiological serum for example having a pH of 7.4). Then a filter-paper washer 17 having a diameter of 20 mm (also damped with physiological serum) is placed above the central cavity 11, then below this washer 17 the filtering membrane 16 (of the "NUCLEPORE" type having a diameter of 13 mm and whose pores have a diameter of $5\mu$). Then the lower block 10 is slid along guide rods 6, and the two blocks are brought together and closed by means of springs 19. Then capillary 2 (having a diameter of 2.5 mm and a length of 6 cm) is filled with the same measuring solvent (physiological serum having a pH of 7.4) which is allowed to flow freely so as to rinse the circuits and the membrane. Then the drain cock 12 is closed, the threeway cock is directed towards the overpressure ballast-receptacle, and an overpressure of about 8 cm of water is created by means of syringe 25. Then the capillary is filled with the same measuring solvent, so that the level of the solvent is about 5 mm above the upper level detector 8. Then the three-way cock 22 is directed towards the "measure" circuit 26. The measuring timer (connected electronically) is automatically reset. The liquid begins to flow: as soon as the level of the liquid reaches the upper detector 8, the timer connected electronically to receiver 8b begins to operate. The measuring timer stops as soon as the level of the liquid reaches the lower detector 9, spaced from detector 8 by 8 mm. Then the flow is stopped by again directing the three-way cock 22 towards the overpressure ballast-receptacle. The time indicated by the timer is noted, capillary 2 is filled with the same meaning solvent and the same operation is begun again 5 consecutive times while noting each time the flow time. The times indicated by the timer are the following:

1st measurement: 0.69 sec
2nd measurement: 0.52 sec
3rd measurement: 0.42 sec
4th measurement: 0.42 sec
5th measurement: 0.42 sec.

The initial flow time of the solvent ts is equal to 0.42 second.

Then the capillary and the lower block are completely drained, without opening the apparatus and without changing the membrane or the filter-paper, and the same operations are begun again but by replacing the measuring solvent with an 8% suspension of red corpuscles (Vol/Vol) in the same solvent (physiological serum at a pH of 7.4). Filtering is carried out three successive times and the three times indicated by the timer are noted.

1st measurement: 0.83 sec
2nd measurement: 0.85 sec
3rd measurement: 0.87 sec.

The initial flow time of the suspension of red corpuscles, tg, is equal to 0.85 sec.

The index of filterability is equal to $$I_f = \frac{tg - ts}{ts \cdot 8} \times 100 = 12$$

When the measurement is finished, the rest of the suspension contained in the capillary is drawn up by means of a syringe, the apparatus is opened and carefully rinsed, whereas the filtering membrane is washed in a sulfochromic mixture so as to be used again.

II. EXAMPLE OF MEASURING THE FILTERABILITY OF THE RED BLOOD CORPUSCLES OF A DIABETIC

The procedure is exactly as described in Example I. We find
$t_s = 0.35$
$t_g = 0.98$
and
$I_f = 22.5$ It follows from the above description that, whatever the methods of implementation, embodiments and modes of application adopted, an apparatus and a process are obtained for determining the rheological properties of biological fluids which present with respect to previously known apparatus and processes having the same aim, important advantages and particularly the advantage of ensuring excellent reproductibility of the measurements, the advantage of great operational simplicity and the advantage of providing an apparatus for a relatively modest cost and allowing measurements to be made for a relatively low cost price.

As is evident from what has gone before, the invention is in nc wise limited to those of its modes of implementation, embodiments and modes of application which have just been described more explicity in what has gone before; it embraces, on the contrary, all variations thereof which may occur to a man skilled in the art, without departing from the scope or spirit of the present invention.

What is claimed is:

1. An apparatus for determining the rheological properties of biological fluids and particularly the deformability of the red corpuscles of the blood, comprising in combination:
    a first upper transparent block containing in its center a capillary having an inner diameter between 1 and 10 mm, which block is provided with two level detectors;
    a second lower transparent block provided with a central duct—facing the capillary of the upper block—inside which duct is housed a droptaking device, said duct being connected on the one hand to a drain circuit and on the other to a pressure-regulating circuit;
    a filtering membrane housed between the two blocks; and
    a frame for holding the apparatus.

2. The apparatus as claimed in claim 1, wherein the filtering membrane rests on a filter-paper whose diameter is slighty greater than that of the membrane.

3. The apparatus according to any one of claims 1 or 2, wherein the two level detectors are housed one below the other and spaced from one another by about 1 to 20 mm.

4. The apparatus as claimed in claim 3, wherein said level detectors are optical detectors formed by a light emitter and a receiving photodiode or phototransistor.

5. The apparatus as claimed in claim 3, wherein the optical detector is formed from an optical fiber connected to a light source and from an optical fiber connected to a receiving photodiode or phototransistor.

6. The apparatus as claimed in claim 4, wherein the optical detector is formed from an optical fiber connected to a light source and from an optical fiber connected to a receiving photodiode or phototransistor.

7. The apparatus as claimed in claim 1, wherein the two level detectors are connected electronically to a timer measuring the filtration time, the upper detector for the starting up, and lower level detector for stopping the timer.

8. The apparatus as claimed in claim 1, wherein the lower block is mobile and slides along two guide rods situated one on each side of the central cavity, said guide rods being held on the one hand on the low part of the upper block, which is made integral with the frame, said low part being bell-shaped with respect to the body of the upper block, and on the other hand by their lower end, on the frame of the apparatus.

9. The apparatus as claimed in claim 8, wherein two springs are each fixed by one of their ends to the lower block, the other end of each of these two springs ending in a hook which engages in two small notches or recesses (one per spring) provided for this purpose in a low bell-shaped part of the upper block.

10. The apparatus as claimed in claim 1, wherein the low part of the capillary is bell-shaped and has a diameter substantially equal to that of the central cavity of the lower block, and slightly less than the diameter of the filtering membrane.

11. The apparatus as claimed in claims 1 or 10, wherein the bell-shaped part of the capillary is provided with seals for holding the filtering membrane.

12. The apparatus as claimed in claims 1 or 10, wherein the upper face of the lower block is provided with a seal for holding the filtering membrane.

13. The apparatus as claimed in claim 1, wherein the drop-taking device is formed from a rod made from glass, a plastic material, metal or similar, integral with the lower block and fixed to the bottom of said lower block by means of a seal and/or ring made from a resilient and sealing material.

14. The apparatus as claimed in claim 13, wherein the drop-taking rod is covered on its upper part which is in contact with the filtering membrane with a strip of filter-paper straddling the end of said rod.

15. The apparatus as claimed in claim 13, wherein the drop-taking rod is formed by a cylinder having laterally therethrough numerous holes which are filled with water-absorbing material.

16. The apparatus as claimed in claim 1, wherein the pressure-regulating circuit comprises a three-way cock, a ballast-receptacle of a capacity between 0.1 and 5 liters, and a syringe, pear-shaped bulb or similar connected to the circuit so as to provide an overpressure in the ballast-receptacle.

17. An apparatus as claimed in claim 16, wherein the pressure-regulating circuit comprises a depression circuit comprising means for creating a depression; and wherein the setting of the three-way cock to the "measure" circuit is connected electronically to the timer for counting down the filtration time so as to reset it automatically.

18. The apparatus as claimed in any one of claims 1, 2, 7, 8, 10, 9, 13, 14, 15 or 16, wherein the pressure-regulating circuit comprises a depression circuit comprising a ballast-receptacle of 0.1 to 5 liters, a syringe, pear-shaped bulb, vacuum pump or similar for creating a depression.

19. The apparatus as claimed in claim 16, wherein the setting of the three-way cock to the "measure" circuit is connected electronically to the timer for counting down the filtration time so as to reset it automatically.

20. The apparatus as claimed in claim 1, wherein the capillary situated at the center of the upper block forms an integral part of the mass of said upper block and is formed in one part therewith during manufacture.

21. A process for determining the rheological properties of biological fluids and particularly a process for measuring the filterability of the red corpuscles of the blood, said process essentially consisting in determining first of all the initial mean flow time of the solvent (physiological serum, plasma or similar), then the initial mean flow time of a volume of the suspension of a given concentration to be examined, and in that the index of the filterability is determined by applying the following formula (9):

$$I_f = \frac{tg - ts}{ts \times H} \tag{9}$$

where
- $I_f$: index of filterability
- $ts$: initial mean flow time of the solvent
- $tg$: initial mean flow time of the suspension of corpuscles to be examined, and
- $H$: mass volume concentration (V/V) of the red blood corpuscles in the suspension or hematocrit.

* * * * *